US006274358B1

(12) United States Patent
Holtz et al.

(10) Patent No.: US 6,274,358 B1
(45) Date of Patent: Aug. 14, 2001

(54) METHOD FOR PROVIDING GREEN NOTE COMPOUNDS

(76) Inventors: Richard Barry Holtz, 3808 Serenity Hills Dr., Vacaville, CA (US) 95688; Michael Jay McCulloch, 296 Loch Lomond Dr., Vacaville, CA (US) 95687; Stephen John Garger, 593 Cottonwood St., Vacaville, CA (US) 95688; Richard King Teague, P.O. Box 194, Merry Hill, NC (US) 27957; Harriet Flannery Phillips, 109 E. Church St., Edenton, NC (US) 27932

( * ) Notice: Subject to any disclaimer, the term of this patent is extended or adjusted under 35 U.S.C. 154(b) by 0 days.

(21) Appl. No.: 08/218,165

(22) Filed: Mar. 25, 1994

(51) Int. Cl.$^7$ ....................................................... C12P 7/04
(52) U.S. Cl. ........................ 435/157; 435/155; 424/774; 424/725; 426/650; 426/655
(58) Field of Search .................................. 435/157, 155; 426/650, 655, 386, 425; 424/195.1, 774, 725

(56) References Cited

U.S. PATENT DOCUMENTS

| | | | |
|---|---|---|---|
| 4,769,243 | 9/1988 | Kanisawa et al. | 426/33 |
| 4,806,379 | 2/1989 | Goers et al. | 426/650 |

OTHER PUBLICATIONS

Garduer, HW., In Flavor Chemistry of Fats and Oils, Ed. Min et al., p. 189–206, 1985.*
Sekiya et al, *Plant and Cell Physiol.*, 25(2) p. 269–280, 1984.*
Olias et al, *J. Agric. Food Chem*, 1993, vol. 41 p. 2368–2373.*
Sigma Catalogue, 1992, p. 74 Dictionary of Gardening 1992, p. 144–145.*
Phillips et al., Phytochemistry, "Partial Purification and Properties of a CIS–3: Trans–2–Enal Isomerase From Cucumber Fruit", vol. 18, pp. 401–404 (1979).
Sekiya et al., Plant Science Letters,"CIS–3 Hexenal and n–Hexanal Formation From Linolenic and Linoleic Acids in Alfalfa Cells Cultured in Vitrol", vol. 10, pp. 165–169 (1977).
Sekiya et al., Phytochemistry, "Fatty Acid Hydroperoxide Lyase in Tobacco Cells Cultured", vol. 23, No. 11, pp. 2439–2443 (1984).
de Lumen et al., Journal of Food Science, "Formation of Volatile Flavor Compounds in Green Beans from Linoleic and Linolenic Acids", vol. 43, pp. 698–702 (1978).
Pfeiffer et al., Crop Science, "Inheritance of a Lipoxygenase–1 Allozyme in Soybean", vol. 33, pp. 691–693, Jul.–Aug. 1993.
Hatanaka et al., Phytochemistry, "Distribution of an Enzyme System Producing cis–3–Hexenal and n–Hexanal from Linolenic and Linolec Acids in Some Plants", vol. 17, pp. 869–872 (1978).

Hatanaka et al., American Chemical Society, Biogeneration of Aromas, "Fatty Acids Hydroperoxide Lyase in Plant Tissues", pp. 167–175 (1986).
Sekiya et al., Phytochemistry, "Distribution of Lipoxygenase and Hydroperoxide Lyase in the Leaves of Various Plant Species", vol. 22, No. 9, pp. 1867–1869 (1983).
Hatanaka, Bull. Inst. Chem. Res., Kyoto Univ., "Biosynthesis of Leaf Alcohol", vol. 61, No. 2, pp. 180–192 (1983).
Gotz–Schmidt, Lebensm–Wiss Technol, vol. 19 (2), "$C_6$–Volatiles in Homogenates from Green Leaves: Localization of Hydroperoxide Lyase Activity", pp. 152–154 (1986).
MacLeod et al., J. Agric. Food Chem., "Formation of (E)–Hex–2–enal and (Z)–Hex–3–en–1–ol by Fresh Leaves of *Brassica oleracea*", vol. 27, No. 3, pp. 469–475 (1979).
Hatanaka et al., Phytochemistry, "Distribution of an Enzyme System Producing cis–3–Hexenal and n–Hexanal from Linolenic and Linoleic Acids in Some Plants", vol. 17, pp. 869–872 (1978).
Saijo et al., Phytochemistry, "Increase of cis–3–Hexen–1–ol Content in Tea Leaves Following Mechical Injury", vol. 14, pp. 181–182 (1975).
Stone et al., Journal of Food Science, "Formation of Aldehydes and Alcohols in Tomato Fruit from U–$^{14}$C–Labeled Linolenic and Linoleic Acids", vol. 40, pp. 1138–1141 (1975).
Hatanaka et al., Agr. Biol. Chem., "Alcohol Dehydrogenase from Thea sinensis Seeds", vol. 38 (10), pp. 1835–1844 (1974).
Hatanaka et al., Phytochemistry, "Formation of cis–3–Hexenal, Trans–2–Hexenal and cis–3–Hexenol in Macerated Thea Sinensis Leaves", vol. 12, pp. 2341–2346 (1973).
Hatanaka et al., Agr. Biol. Chem., "Purification and Properties of Alcohol Dehydrogenase from Tea Seeds", vol. 36, No. 11, pp. 2033–2035 (1972).
Hatanaka et al., Agr. Biol. Chem., "Photochemical Isomerization of Leaf Aldehyde", vol. 36, No. 7, pp. 1263–1264 (1972).
Major et al., Phytochemistry, "Formation of 2–Hexenal from Linolenic Acid by Macerated Ginkgo Leaves", vol. 11, pp. 611–617 (1972).

* cited by examiner

*Primary Examiner*—Irene Marx

(57) ABSTRACT

Green note compound, such as cis-3-hexen-1-ol, is provided by subjecting linolenic acid and a fresh watermelon foliage to shearing in the presence of an aqueous liquid and yeast. Enzymes within the plant material (i.e., lipoxygenase and hydroperoxide lyase) and the yeast act to cause the linolenic acid to be converted to green note alcohol at a relatively high yield. Green note compound can be provided naturally using a continuous or batch process.

20 Claims, No Drawings

METHOD FOR PROVIDING GREEN NOTE COMPOUNDS

BACKGROUND OF THE INVENTION

The present invention relates to flavors and fragrances, and in particular to methods for providing flavorgenic alcohols and aldehydes using plant tissue.

Leaf alcohol (i.e., cis-3-hexen-1-ol) and leaf aldehyde (i.e., trans-2-hexenal) are present in a wide variety of fresh leaves, vegetables and fruits. These compounds are responsible for a so-called "green odor", "green aroma", "fresh note" or "green note". Related compounds present in many plants include trans-2-hexenol, cis-2-hexenol, trans-3-hexenol, 1-hexanol, 1-hexanal and cis-3-hexenal. Green note compounds and uses thereof are set forth by Morris, *Perfumer & Flavorist*, Vol. 6, No. 1 (1981) and Clark, *Perfumer & Flavorist*, Vol. 15 (1990). Green note compounds exhibit organoleptic characteristics which can be characterized as fresh or grassy in nature. Such compounds can be used to sharpen and enhance flavored products, such as those products having fruit flavors.

Green note compounds have been isolated from plants or chemically synthesized, as reported by Bedoukian, *Amer. Perf.* Vol. 78, p. 31 (1963) and U.S. Pat. No. 3,839,457 to Jouffret. Green note compounds are present in plant essential oils (e.g., sage, citrus and mint), and have been obtained by steam distillation of plant material followed by fractional distillation or "topping" techniques. Green note compounds also have been biosynthetically produced, as reported by Muller et al, *Adv. Flav. Res. Tech. Symposium* (1993); Hatanaka el al, *Phytochem.*, Vol. 17, p. 869 (1978); Hatanaka, *Bull. Inst. Chem. Res., Kyoto Univ.*, Vol. 61, p. 180 (1983); Lumen et al., *J.Food Sci.*, Vol. 43, p. 698 (1978); Hatanaka et al., *Phytochem.*, Vol. 17, p. 869 (1978); Sekiya et al., *Phytochem.*, Vol. 23, p. 2439 (1984); Hatanaka et al., *ACS Symposium Biogeneration of Aromas* (1985); French Patent Application No. 2,652,587; U.S. Pat. No. 4,769,243 to Kanisawa et al and U.S. Pat. No. 4,806,379 to Goers et al; and WO 93/24,644. The biosynthetic reaction involving the unsaturated C-6 hydroperoxydismutation of linolenic acid is carried out using a series of enzymatic steps. In particular, lipoxygenase forms a hydroperoxide moiety at a double bond of linolenic acid. The hydroperoxide lyase cleaves the hydroperoxide to produce a C-6 unsaturated aldehyde, in particular, cis-3-hexen-1-al. Then, aldehyde isomerase, when present in the plant material and under certain conditions, catalyzes the formation of a trans-2-hexenal from the cis-3-hexen-1-al. Cis-3-hexen-1-ol and other green note alcohols are formed by the action of alcohol dehydrogenase, which reduces the aldehydes to alcohols.

It would be highly desirable to provide an efficient and effective method for biosynthetically producing natural green note compounds, such as cis-3-hexen-1-ol. In particular, it would be highly desirable to provide green note compounds, such as shortchain saturated and unsaturated alcohols and aldehydes, which result from the enzymatic oxidation of a fatty acid substrate.

SUMMARY OF THE INVENTION

The present invention relates to a method for providing green note compounds. The process, in one aspect, involves the steps of:

a) providing unsaturated fatty acid, such as linolenic acid;
b) providing plant biomass, such as fresh watermelon foliage, having active levels of lipoxygenase and hydroperoxide lyase enzymes;
c) providing alcohol dehydrogenase, such as in the form of active yeast;
d) providing a mixture by contacting the plant biomass and unsaturated fatty acid in the presence of the alcohol dehydrogenase and an aqueous liquid under conditions sufficient to:
   i) provide release of lipoxygenase and hydroperoxide lyase from the plant biomass, and
   ii) provide reaction of the fatty acid with the lipoxygenase, hydroperoxide lyase and alcohol dehydrogenase to provide a green note compound;
e) collecting aqueous phase containing green note compound; and
f) separating green note compound from the aqueous phase.

The plant biomass (i.e., plant material), unsaturated fatty acid and alcohol dehydrogenase are combined in the presence of an aqueous liquid. The ingredients most preferably are contacted with one another in an essentially simultaneous fashion; or the plant material is combined with a mixture of unsaturated fatty acid, a source of alcohol dehydrogenase and water. In a highly preferred aspect, the ingredients are combined in a continuous manner in controlled amounts. The ingredients most preferably are subjected to high shear agitation. As such, the plant material is macerated in order to release the enzymes and provide for mixing of ingredients involved in the biochemical reaction. Thus, the unsaturated fatty acid is converted to a green note compound. That is, the lipoxygenase and fatty acid interact to form a fatty acid hydroperoxide, which is cleaved by the action of the hydroperoxide lyase to form an aldehyde, which is converted to an alcohol by the action of the alcohol dehydrogenase. As such, the biosynthesis of the green note compound occurs in such a manner so as to result in a high yield of that compound relative to the amount of plant material employed. Green note compounds produced according to the process steps of this aspect of the present invention include cis-3-hexen-1-ol as the primary green note compound component.

DETAILED DESCRIPTION OF THE PREFERRED EMBODIMENTS

Green note compounds capable of being provided using the process of the present invention can vary. Exemplary compounds include cis-3-hexen-1-ol, trans-2-hexen-1-ol, n-hexanal, trans-3-hexen-1-ol, cis-3-hexenal, trans-2-hexenal, trans-3-hexenal, 1-hexanol, cis-3-penten-3-ol and cis-2-penten-1-ol. Preferred green note compounds include cis-3-hexen-1-ol, trans-2-hexenol and trans-2-hexenal as primary green note components. When the fatty acid is linolenic acid, and all of the ingredients are combined in an essentially simultaneous fashion, the green note compounds consist predominantly of cis-3-hexen-1-ol; and depending upon the purity of that acid (i.e., the presence of certain amounts of other fatty acids), relatively minor amounts of other green note compounds (e.g., trans-2-hexenal and 1-hexanol) can be produced. When the alcohol dehydrogenase is combined with the other ingredients after those other ingredients have been combined, the green note compounds which result have a tendency to consist of complex mixtures of green note compounds, which mixtures can vary depending upon factors such as selection of fatty acid, amount of yeast employed, and timing of yeast addition to the other ingredients of the biochemical reaction. Typical green note compounds are volatile, and are highly flavorful and aromatic. Desired green note compounds are those which exhibit fresh, green and leafy aroma and flavor properties and characteristics.

Plant materials useful in carrying out the process of the present invention can vary. Plants having relatively highly accessible amounts of enzymes (e.g., lipoxygenase and hydroperoxide lyase) are preferred. The plant material also can contain aldehyde isomerase enzyme, which has the effect of transforming an aldehyde in a cis form to a trans form. Typically, the amount of aldehyde isomerase in most plant materials useful in accordance with the present invention is sufficient to provide transformation of about 2 to about 50 percent of cis-aldehyde to trans-aldehyde. Plant materials such as alfalfa have relatively high levels of aldehyde isomerase, while plant materials such as watermelon foliage have relatively low levels of aldehyde isomerase. The plant material can be provided by a single plant variety or by a mixture of two or more plant types, each of which has a desirable level of lipoxygenase, hydroperoxide lyase or aldehyde isomerase. For example, soybeans which have not been heat treated, defatted or solvent treated can have relatively high levels of lipoxygenase; and warm weather-grown watermelon vine and cold weather-grown spinach have relatively high levels of hydroperoxide lyase. If desired, various portions of different types of plants can be mixed together (e.g., fruit from at least one type of plant can be combined with foliage of at least one other type of plant). It is also desirable to select plants that do not provide undesirable flavor or aroma characteristics to the ultimate green note composition which is isolated.

Representative plant materials are set forth by Hatanaka, *Bull. Inst. Chem. Res., Kyoto Univ.*, Vol. 61, p. 180 (1983); Sekiya et al, *Phytochem.*, Vol. 22, p. 1869 (1983); Hatanaka et al, ACS Symposium Biogeneration of Aromas (1985); Gotz-Schmidt et al, *Lebensm. Wiss. Tech.*, Vol. 19, p. 152 (1986). Desirable plant materials which incorporate hydroperoxide lyase and/or lipoxygenase enzymes include vegetative growth or foliage (e.g., seedlings, leaves and vines) of cantaloupe (*Cucumis melo*) (e.g., cvs. 'Hale's Best Jumbo', 'HMX Western', 'Hearts of Gold'), watermelon (*Citrullus lanatus*) (e.g., cvs. 'Charleston Gray', 'Crimson Sweet', 'Sugar Baby', 'Sultan'), strawberry (*Fragaria Xananassa*), cucumber (*Cucumis saetivus*), kidney bean (*Phaseolus vulgaris*), tomato (*Lycopersicon lycopersicum*), honeydew melon (*Cucumis melo*) (e.g., cvs. 'Morning Ice') and amaranths (*Amaranthus*) (e.g.,pigweed foliage, such as *Amaranthus retroflexus*); the leaves or tops of radish (*Raphanus sativus*); alfalfa (*Medicago sativa*); kidney bean (*Phaseolus vulgaris*), hanover salad (*Brassica napus*), rutabaga (*Brassica napus*), spinach (*Spinacia oleracea*), turnip (*Brassica rapa*), Chinese cabbage (*Brassica rapa*) (e.g., cvs. 'Pe-Tsai'), mustard (*Brassica juncea*) (e.g., 'Florida Broadleaf', 'Old Fashion'), salad greens or mixed greens (e.g., mixtures of turnip, mustard, kale, and the like), false acacia (*Robinia pseudoacacia*), clary sage (*Salvia sclarea*) and tea (*Thea sinensis*); and the fruit or seed of soybean, green bean, strawberry, kidney bean or snap bean; and processed plant materials such as soy flour. The most desirable plant materials are those that combine high levels of enzyme acitivity and high biomass potential; and are adaptable to standard agromonic production methods and processing conditions.

The manner in which the plant is grown can vary. The plant can be grown outdoors or in a greenhouse. The growing conditions can vary, as well as can growing location, soil type, growing season, and the like. The growing season can vary, depending upon the particular plant and the type of biomass desired (e.g., biomass in the form of green leaf or fruit). For example, watermelon vegetative biomass can be grown during warm weather months, while cole crops can be grown early or late in the growing season during cooler time frames. If desired, plants which are harvested for biomass purposes can be cultivated in a closely grown fashion whereby plants are grown in a relatively high density in a particular growing area. For certain plants, such as watermelon, it is desirable to employ agronomic techniques so as to achieve maximum green leaf growth (i.e., maximum green leaf biomass), which typically occurs prior to the time that fruit begins to form.

Techniques can be employed in order to provide plants having enhanced enzyme levels. Plants can be bred to have high levels of the desired enzymes. Recombinant DNA techniques can be employed to produce transgenic plants having high levels of enzymes. See, Deng et al, *Planta*, Vol. 187, p. 203 (1992). Plants can be transfected with viral vectors capable of enhancing enzyme production. See, Kumagai et al, *Proc. Nat. Acad. Sci.*, Vol. 90, p. 427 (1993). Plants can be induced to produce enhanced levels of enzymes (e.g., methyl jasmonate can induce the production of lipoxygenase in soybean, and rice blast infection can induce the production of lipoxygenase in tomato leaves). See, Crimes et al, *Plant Physiol.*, Vol. 100, p. 443 (1992) and Kato et at, *Biosci. Biotch. Biochem.*, Vol. 56, p. 373 (1992). Growing conditions, such as water deficit and plant wounding, can also have an effect on enzyme production. See, Bell et al, *Mol. Gen. Genet.*, Vol. 47, p.456 (1991).

The manner in which the plant is harvested can vary, but most preferably is such that the enzymes usefull for the biosynthesis of the green note compounds remain present in the plant in order that an active level of those enzymes remains desirably high during the period of the biosynthetic reaction. Periods of harvest can vary from crop to crop depending upon factors such as the biomass potential and developmental stage of a particular plant, and the timings of multiple cuttings after regrowth. As such, for plants such as watermelon, the whole plant typically is harvested by severing the stem just above ground level, preferably prior to the time that fruit begins to form. Plants can be harvested using mechanized harvesting equipment suitable for the type of plant material being harvested. Such equipment can include a Porter-Way greens harvester. Harvested plant material having a form of vine can be chopped or otherwise subdivided to some degree (e.g., into lengths of about 8 to about 12 inches) during harvest in order to prevent an entangled mass of plant material which tends to be difficult to meter and process during processing steps associated with the bioreaction.

The enzymes in the harvested plant can have a tendency to become inactive (i.e., lose ability to undergo the desired biochemical reaction with the unsaturated fatty acid) if the harvested plant is not treated properly. It is desirable to keep the plant in tact as much as possible after harvesting. As such, the plant most preferably is not chopped or otherwise broken to any significant degree until very near the time that the plant is used in the biochemical reaction of the present invention. That is, inactivity of the enzymes can occur very rapidly after the plant is harvested, and as such, it is desirable to provide controlled storage and handling conditions, or to use the harvested plant as quickly as possible. It is also desirable to keep the plant cool and to avoid letting the plant become dry prior to use thereof according to the present invention. It is desirable to avoid adversely affecting the activities of the enzymes within the plant material by subjecting that material to freezing temperatures or to temperatures above 45° C. Typically, certain plant materials are employed within 6 hours, usually within 4 hours after harvest. However, it is possible to store certain plant materials under cool, moist conditions (e.g., about 2° C. to about 10° C., preferably about 3° C. to about 4° C.) for several days (e.g., up to about 7 days, but usually up to about 3 days) after harvest without significant loss of enzymatic activity. It is most desirable to use fresh plant material. By fresh plant material is meant a plant material that overall can be considered green, succulent, turgid, not wilted due to loss of original moisture, not browned or oxidized, and not overly bruised due to actions such as squeezing.

The unsaturated fatty acid can vary. The unsaturated fatty acid is provided in a free acid form (e.g., in a carboxylic acid or salt form), as opposed to an esterified (e.g., triacylglycerol) form. Examples are oleic acid, linoleic acid, linolenic acid (alpha and gamma forms), arachidonic acid, eicosapentaenoic acid and ricinoleic acid. The unsaturated fatty acid can also be provided by reacting an oil (e.g., vegetable oils such as linseed oil, safflower oil and soya oil) with a lipase or using high pressure steam hydrolysis conditions to hydrolyze triacylglycerols in that oil to free fatty acid and glycerol. See, for example, U.S. Pat. No. 4,769,243 to Kanisawa et al. Unsaturated fatty acids also can be provided by chemical saponification of fats and oils using base. Techniques for providing unsaturated fatty acids from fats and oils will be apparent to the skilled artisan. The unsaturated fatty acid can be employed as a mixture of acids (i.e., as a formulation of relatively low purity of one particular fatty acid). However, the unsaturated fatty acid can also be employed in a relatively pure form (e.g., having a purity of greater than about 90 weight percent, and even greater than about 95 weight percent). Unsaturated fatty acids of high purity tend to provide for green note alcohols of high purity (e.g., linolenic acid of high purity tends to yield a green note composition that is high in purity of cis-3-hexen-1-ol).

The amount of unsaturated fatty acid relative to the amount of plant material can vary, and depends upon factors such as the level of enzyme in the plant material. Typically, amounts of acid are in slight excess to the enzyme level in the plant material. For example, for linolenic acid, the amount of acid ranges from about 5 to about 10, generally about 7 to about 9, mg linolenic acid per gram of plant material.

Active yeast is provided. Active or fresh yeast has the capability of converting an aldehyde to an alcohol. The yeast is a source of an alcohol dehydrogenase, and nicotine adenine dinucleotide (NADH) which provides biological reducing power (i.e., an ability to cause a conversion of an aldehyde to an alcohol). An example is active baker's yeast. The yeast most preferably has a cream or cake form, and is used in a cream slurry or wet cake form. If desired, the yeast can be combined with materials such as sugars (e.g., glucose) or molasses in amounts sufficient to enhance the enzymatic activity of the alcohol dehydrogenase. The yeast is employed in order to provide a source of alcohol dehydrogenase which causes reduction of the aldehydes formed by the action of hydroperoxide lyase to the corresponding alcohol. Yeast incorporating recombinant DNA expression systems can be employed as sources of increased levels of alcohol dehydrogenase and to provide biological reducing power.

The amount of yeast employed can vary, and depends upon the desired transformation of aldehyde to alcohol. For example, an excess of yeast can be employed in order to provide for nearly complete conversion of aldehyde to alcohol. Normally, the amount, by weight, of yeast employed does not exceed 30 times, and usually is about 15 to about 20 times, that of the amount of the unsaturated fatty acid employed.

The unsaturated fatty acid, plant material and yeast are mixed or otherwise blended together homogeneously in proper proportion in the presence of an aqueous liquid. The aqueous liquid is water (e.g., deionized water or tap water) and can include water containing additives, such as buffers which can act to maintain an optimum pH within the reaction mixture for effective action of the enzymes. Typically, the aqueous liquid is provided at a temperature of about 10° C. to about 25° C. The plant material can be chopped (e.g., to a size of about 3 inches by about 3 inches, or to a size as large as about 6 inches by about 12 inches) immediately prior to the aforementioned blending. Such chopping or subdivision insures accurate addition of plant biomass to the shearing device in a commercial scale process when equipment such as a weigh-belt feeder is employed. However, the degree of chopping is not so great (e.g., so as to be considered dicing) in order that the cellular disruption of the biomass is not significant and the enzymes do not experience an undesirable release from the biomass prior to the time that such enzymes are desired to be used. As such, the enzymes are active when contacted with the fatty acid in order to carry out the biochemical reaction upon the fatty acid. Thus, high levels of active enzymes are desirable (i.e., due to a high level in the plant material and/or due to the use of a large amount of plant material) in order to cause a large amount of fatty acid to undergo the desired bioreaction. Active enzymes have the ability to cause bioreaction upon the fatty acid. Enzymes within the cells of the biomass tend to become inactivated very rapidly upon release from those cells as a result of action of oxidation, proteases and other inhibitors present within the plant material.

In the preferred aspect of the present invention, all of the ingredient materials are added together simultaneously, as opposed to in a step-wise fashion. That is, in within a matter of seconds, the plant material is combined with the fatty acid and yeast in an aqueous slurry; or the plant material, fatty acid and yeast are combined at essentially the same time in an aqueous environment. In a continuous process, the fatty acid, plant material and yeast are metered into a mixing region along with the aqueous liquid in controlled amounts under conditions such that the desired enzymes are released from the plant material and such that the biochemical reaction can occur, As such, the enzymes are released from the plant material in the presence of the yeast and in the presence of the unsaturated fatty acid. As a result, green note compounds predominantly having a cis-3-hexen-1-ol character and type are formed. When the yeast is added to the aqueous slurry of plant material and unsaturated fatty acid, normally in about 5 to about 60 minutes after the reaction of enzymes in the plant material and acid is initiated, the resulting green note compounds consist of complex mixtures of significant amounts of green note aldehydes and alcohols.

Typically, the reaction mixture is maintained above 15° C. and preferably above about 20° C. It is desirable to maintain the mixture below 45° C., and most desirably below 40° C. in order to ensure significant activity of the lipoxygenase and hydroperoxide lyase. Preferably, the mixture is maintained at a temperature which does not exceed about 35° C., and most preferably is below about 30° C.

The amount of aqueous liquid employed can vary. The amount of aqueous liquid is employed in an amount sufficient to provide for ease of shearing and hence minimize temperature increases that provide an attendant destruction or inactivation of the enzymes. However, it is also desirable to maintain the amount of aqueous liquid sufficiently low in order to allow for greater ease in later processing steps when the ultimate green note product is separated from that liquid for isolation. Ratios of aqueous liquid to plant material can range from about 2:1 to about 7:1, with about 3:1 to about 6:1 being preferred, and with about 5:1 being generally preferred.

Cell disruption conditions are provided in order to facilitate release of lipoxygenase from the water soluble fraction of the cytoplasmic region of the cells which make up the biomass, and hydroperoxide lyase from the chloroplast membrane region of the cells which make up the biomass. Cell disruption most preferably is provided by shearing action. That is, shearing provides a maceration of the cell to expose the enzymes, and also provides rapid release of the enzymes from the cell material in order to effectively provide the enzymes in an environment for the desired reaction. Cellular disruption or tissue disruption resulting from the action of high shear exposes the intracellular enzymes of the biomass to the fatty acid and the active yeast in an essentially instantaneous fashion. Shearing provides rapid release of the lipoxygenase and hydroperoxide lyase enzymes from the plant material in order that those enzymes can react with the fatty acid in order to efficiently produce cis-3-hexenal, which is in turn converted to cis-3-hexen-1-ol by the alcohol dehydrogenase.

By shearing or high shear is meant rapid agitation of the processed slurry in order to provide or approach homogenization of that slurry. Shearing can be provided by fast moving mixer blades (e.g., moving in excess of about 3000 rpm) or having high blade tip speeds (i.e., in excess of about 9000 ft./second). Shearing conditions are sufficient to subject the total volume of the slurry being processed to conditions of shear stress and strain. In a continuously fed high shear device, such as a Reitz disintegrator, cell disruption can be carried out in less than about 30 seconds, often in less than about 15 seconds, while total shear time typically is less than 5 minutes. In a batch-wise shearing device, such as a blender, the mixture typically is agitated for about 0.5 to about 5 minutes, usually about 1 to about 4 minutes. If desired, a bipolar surfactant (e.g., Lecithin or Tween 20) can be incorporated into the mixture during shearing in order to assist in release of the hydroperoxide lyase from the chloroplasts of the cells of the plant material and to assist in improving the oil/water interface of the enzyme with fatty acid. Shearing can be carried out using high shear kitchen-type blenders (e.g., a Waring blender), a Reitz Mill, a Reitz Disintegrator, a Fitzmill mixer, a Hobart mixer, a Breddo mixer, or like high shear mixing devices; an ultrasonic mixing device; or an impaction and attrition device such as a Kady Mill. It is also desirable to couple two mixing devices, such as a Reitz disintegrator and a Kady mill or a Reitz disintegrator and a Breddo mixer, to provide optimal shearing resulting in maximal contact of unsaturated fatty acid and released enzymes. Such high shear devices provide rapid maceration of the plant material so as to provide rapid and maximum release of the enzymes under aerated conditions, and also provide for conditions of rapid interaction (i.e., mixing) of the components of the reaction mixture.

The liquid and pulp portions of the resulting mixture are separated from one another. Separation of pulp and other solids from the aqueous liquid acts to facilitate removal of green note compounds from the aqueous liquid. Centrifugation (e.g., using a disc-stack, decanter, or similar device) can be employed. Filtration (e.g., using a rotary vacuum filter, or similar device) can be employed. Typically, such separation is carried out by screening water insoluble solids from the aqueous liquid. Screening or dewatering devices include a Sweco screen, a Rotex screen or a Hydrosieve. If desired, the mixture can be pressed to remove a further amount of the liquid portion from pulp portion. A Reitz Press or similar equipment can be used to further separate the liquid and pulp portions from one another. As such, aqueous liquid containing green note compound is collected.

The liquid portion is allowed to undergo a reaction, set or incubation time. During such time, the reaction mixture can be allowed to set for an extended period without mixing or agitation, or the mixture can be agitated. Preferably, the shearing (i.e., plant tissue disruption) and extended set (i.e., reaction) periods are carried out under ambient atmosphere and at temperatures which approximate ambient temperature. The reaction time typically lasts at least 15 minutes, often ranges from about 20 to about 30 minutes, frequently does not exceed about 6 hours, and usually does not exceed about 60 minutes. Conditions of temperature and pH of the liquid can be controlled during the extended reaction time, however, the temperature is often ambient temperature and the pH is not altered after the mixing period. The extended reaction step can be carried out without purposefully aerating the mixture, without introducing supplemental oxygen into the mixture, or without carrying out the process steps under inert (e.g., nitrogen) atmosphere. Typically, the initial shearing action which is provided in ambient atmosphere allows for adequate introduction of oxygen into the mixture.

The green note compounds which are within the aqueous liquid are separated from the aqueous liquid and most preferably are isolated. That is, the green note compounds are provided in a relatively concentrated or essentially pure form. Green note compounds can be isolated so as to have purities of greater than about 90, often greater than about 95, frequently greater than about 98, and even greater than about 99 percent, on a weight basis. The manner in which the green note compounds are separated from a significant amount of the aqueous liquid in which it is provided can vary.

The aqueous liquid containing the green note compounds can be subjected to distillation so as to obtain a distillate containing green note compounds. Such distillation techniques typically involve distilling the aqueous liquid under vacuum (e.g., at 25° C. to 60° C., and 10 to 150 mm Hg). In such a manner, collection as distillate of about ⅓ or more of the volume of the liquid which is subjected to distillation typically provides within the distillate greater than 98 percent of the green note compounds present in the starting liquid. For example, collection of distillate of about ½ of the volume of the aqueous liquid subjected to rotary vacuum distillation at 55° C. and 15 mm Hg typically provides essentially all of the green note compounds subjected to distillation as distillate. Under such conditions, the distillate is a mixture of green note compounds and water, and the green note compounds frequently are present in the water in an amount of about 500 ppm. The condensate so provided can be passed through a collection column (e.g., a column containing particles of activated carbon, or a column containing hydrophobic macroporous ion exchange resin particles such as Amberlite XAD-2 from Rohm & Haas) so that green note compounds are collected on the substrate material within the column. The green note compounds then can be removed from the collection column using an eluting solvent (e.g., ethyl acetate, diethyl ether, hexane, chloroform, methanol or ethanol); and isolated to a desired purity by fractional distillation techniques (e.g., ambient, vacuum or steam distillation techniques) using a high efficiency distillation column. A mixture of ethanol, water and green note compound can be distilled so as to provide fractional distillation, and hence separation of the green note compound from the other liquids. Alternatively, the green note compound can be removed from the collection column using a supercritical fluid (e.g., supercritical carbon dioxide at 38° C. to 45° C., and 340 to 400 bar pressure); and isolated to high purity by evaporating liquid carbon dioxide under ambient pressure conditions. Alternatively, the green note compound can be removed from the collection column using thermal desorption techniques, and isolated by condensing the vaporized compound.

The process of the present invention provides several advantages. The process provides an efficient and effective manner or method for producing green note compounds at relatively high yield and of high purity. The process provides yield of green note compound (e.g., including cis-3-hexen-1-ol) in excess of 400, preferably in excess of 600, more preferably in excess of 700, and most preferably in excess of 800 ug/g plant material employed. The process also provides for yields of green note compound (e.g., including cis-3-hexen-1-ol) in excess of 900 ug/g plant material employed, frequently in excess of 1000 ug/g plant material employed, and even in excess of 1100 ug/g plant material employed. The process provides for control of reaction conditions and ingredients in order that the relative amounts of green note compounds can be controlled. When the unsaturated fatty acid employed according to the process of the present invention is predominantly linolenic acid, the compostion of the green note compound mixture preferably is greater than about 65 percent, often is greater than about 70 percent, and frequently is greater than 75 percent, cis-3-hexen-1-ol, relative to the weight of all green note compounds obtained. For unsaturated fatty acid having a relatively high level of linolenic acid, the green note product obtained often can be more than about 80 percent, and even greater than 90 percent, cis-3-hexen-1-ol, relative to the weight of all green note compounds obtained. When the unsaturated fatty acid employed according to the process of the present invention is essentially pure linolenic acid (e.g., having a purity of greater than about 95 weight percent), the green note product obtained often is more than about 99 percent cis-3-hexen-1-ol.

The following examples are provided in other to further illustrate the invention but should not be construed as limiting the scope thereof. Unless otherwise noted, all parts and percentages are by weight.

EXAMPLE 1

Into as Osterizer kitchen blender is charged 100 g of a plant material, 14.6 g of a Red Star cake yeast, 1.65 ml linolenic acid (55%, 18:3) available from Eastman Chemical Co., and 500 ml deionized water. The plant material is fresh *Amaranthus retroflexus* collected from the leafy, distal 12 inches of a field grown specimen bearing immature fruit, and cut into 2 to 3 inch long pieces using hand clippers.

The mixture in the blender, which is about room temperature, is homogenized by operating the blender at high speed setting for about 2 minutes. The resulting homogenate then is filtered through 4 layers of cheese cloth. The filtrate then is allowed to set for 1 hour. The filtrate then is swirled gently, and a 4 ml aliquot is drawn. To the aliquot is mixed 4 ml ethyl acetate, and the resulting mixture is centrifuged. The organic fraction is analyzed for cis-3-hexen-1-ol using gas chromatographic analysis techniques. The amount of cis-3-hexen-1-ol in the reaction mixture is determined to be 990 ug/g fresh plant material processed.

EXAMPLE 2

Green note compound is produced in a continuous manner in commercial scale amounts in the following manner. Seed of mixed greens is composed of seeds of turnip (*Brassica rapa* 'Seven Top'), kale (*Brassica napus* and *B. napus* 'Dwarf Siberian Improved'), and mustard (*Brassica juncea* 'Florida Broadleaf', 'Southern Giant Curled'and 'Old Fashion'). The seeds are sown with a Stan Hay planter, 5 rows per 50 inch raised bed. The seeds are sown in sandy loam soil in eastern North Carolina. The plant foliage is cut 66 days after planting using a Porter Way greens harvester, and transported by live bottom or dump wagon to a processing area. Within 4 hours from harvest, the harvested greens are fed using a drag-link conveyer to a cutting region where the greens are cut using cutting blades into 6–12 inch pieces. The fresh greens then are transported to a weighing area (i.e., a weigh-belt feeder) so as to cross a Thayer scale at a rate of 800 lb/hr. The greens are macerated using a Reitz Disintegrator (i.e., in about $\frac{1}{10}$ second, but in less than 1 second). Also metered into the Reitz Disintegrator simultaneously with the greens is tap water at about 18° to 20° C. at a rate of 4000 lb/hr., 11.78 lb/hr of linolenic acid (55%, 18:3) from Eastman Chemical Co., and 176.4 lb/hr of a fresh active yeast slurry. The active yeast slurry is provided by mixing 117.6 lb of Red Star cake yeast into 58.8 lb of well water. The metered ingredients are contacted with one another essentially simultaneously. That is, the ingredients are contacted with each other in a simultaneous fashion in controlled amounts relative to one another in a manner which involves continuous feeding and removal of those ingredients from the mixing region. The resulting homogenized mixture is pumped to a 50 gallon Breddo mixer with a flow rate adjusted to give a 5 minute, on average, retention or set time in the shearing mixer. The slurry is passed through a Sweco screen of (e.g. of 24 to 80 mesh Tyler sieve) and the liquid is collected. The moist solid mixture then is fed into a Reitz press and liquid is collected. The pulp, which has a moisture content of about 66 percent, is discarded. The liquid from the pressing and screening operations (which has a dissolved/dispersed solids content of about 2 percent) is collected (i.e., after dewatering and after pressing). The liquid is allowed to set for about 1 hour at about 25° C.

To a 4 ml aliquot of the liquid is mixed 4 ml ethyl acetate, and the resulting mixture is centrifuged. The organic fraction is analyzed for cis-3-hexen-1-ol using gas chromatographic analysis techniques. The amount of cis-3-hexen-1-ol in the reaction mixture is determined to be 966 ug/g fresh plant material processed.

The liquid then is fed to a Votator type thin film evaporator of 1 square foot area operated at a steam pressure of 50 psi on the evaporator shell. The liquid feed is about 0.3 gal./min. The overall system is operated at a vacuum of 23 inches Hg with the evaporator overhead vapor at 53° C. Alternatively, the liquid is evaporated under vacuum as a whole batch using a steam jacketed vessel. The liquid in the vessel is maintained at about 41° C. by controlling the steam pressure within the jacket at about 50 psi. The overhead vapor is about 37° C. when the vacuum is 26.8 inches Hg.

The distillate from the wiped film evaporator is percolated through an absorbent consisting of activated carbon or macroporous resin to absorb the volatile organic constituents. After collection the volatiles are eluted with ethanol. The collected product in ethanol is further distilled to a desired concentration of green note compound in ethanol (e.g., a concentration of between 25% and 90% cis-3-hexen-1-ol in ethanol).

EXAMPLE 3

Into a Waring Blender at room temperature is mixed 30 g fresh field grown Charleston Gray watermelon leaf and vine, 150 ml tap water, 5 g Fleischmann's cake yeast, and 250 mg linolenic acid (97%, 18:3) obtained from Sigma Chemical. The ingredients are subjected to shearing for 2 minutes at high speed setting. The resulting mixture exhibits a pH of 5.68 and a temperature of 35.5° C. The mixture is filtered through 4 layers of cheese cloth, and the green filtrate which is collected is allowed to set for 1 hour at 23° C. Then, 2 ml of the filtrate is extracted with 2 ml diethylether. The amount of cis-3-hexen-1-ol in the reaction mixture is determined by gas chromatographic analysis to be 1010 ug per gram of fresh plant material processed. Similar ingredients, similar in relative amount and similarly sheared for 1 minute and 3 minutes yielded amounts of cis-3-hexen-1-ol of 843 and 847 ug per gram of fresh plant material processed, respectively. The temperature of the mixture sheared for 1 minute reaches 29° C., while that of the mixture sheared for 3 minutes reaches 37.5° C.

EXAMPLE 4

Into a Waring Blender at room temperature is mixed 38 g fresh field grown Charleston Gray watermelon leaf and vine, 150 ml tap water, 6.25 g Fleischmann's cake yeast, and 313 mg linolenic acid (97%, 18:3) obtained from Sigma Chemical.

The ingredients are subjected to shearing for 2 minutes at high speed setting. The resulting mixture exhibits a pH of 5.85 and a temperature of 32° C. The mixture is filtered through 4 layers of cheese cloth, and the green filtrate which is collected is allowed to set for 1 hour at 23° C. Then, 2 ml of the filtrate is extracted with 2 ml diethylether. The amount of cis-3-hexen-1-ol in the reaction mixture is determined by gas chromatographic analysis to be 1062 ug per gram of fresh plant material processed. Similar ingredients, similar in relative amount and similarly sheared for 1 minute and 3 minutes yielded amounts of cis-3-hexenol of 899 and 852 ug per gram of fresh plant material processed, respectively. The temperature of the mixture sheared for 1 minute reaches 28.5° C., while that of the mixture sheared for 3 minutes reaches 39° C.

EXAMPLE 5

Into a Waring Blender at room temperature is mixed 50 g fresh field grown Charleston Gray watermelon foliage, 150 ml tap water, 8.3 g Fleischmann's cake yeast, and 417 mg linolenic acid (97%, 18:3) obtained from Sigma Chemical. The ingredients are subjected to shearing for 2 minutes at high speed setting. The resulting mixture exhibits a pH of 5.88 and a temperature of 34° C. The mixture is filtered through 4 layers of cheese cloth, and the green filtrate which is collected is allowed to set for 1 hour at 23° C. Then, 2 ml of the filtrate is extracted with 2 ml diethylether. The amount of cis-3-hexen-1-ol in the reaction mixture is determined by gas chromatographic analysis to be 963 ug per gram of fresh vine processed. Similar ingredients, similar in relative amount and similarly sheared for 1 minute and 3 minutes yielded amounts of cis-3-hexen-1-ol of 802 and 466 ug per gram of fresh plant material processed, respectively. The temperature of the mixture sheared for 1 minute reaches 29° C., while that of the mixture sheared for 3 minutes reaches 40° C.

EXAMPLE 6

Into a Waring Blender at room temperature is mixed 20 g fresh field grown alfalfa, 200 ml tap water, a yeast pellet of about 1 g obtained from a 50 ml culture of *Saccharomyces cerevisiae* 1403-ER40 obtained from University of California, Davis, and 200 mg linolenic acid (97%, 18:3) obtained from Sigma Chemical which is added during shearing. The ingredients are subjected to shearing for 1 minute at high speed setting. The mixture is strained through cheese cloth, and the green filtrate which is collected is allowed to set under stirring for 15 minutes at room temperature. The amount of cis-3-hexenol in the reaction mixture is determined by gas chromatographic analysis to be 71 percent cis-3-hexenol, 29 percent hexenals, no detectable trans-2-hexenol and no detectable 1-hexanol.

Similar ingredients, similar in relative amount and similarly sheared for 1 minute, but using 200 mg linoleic acid from Sigma Chemical (97% pure) rather than linolenic acid, yields about 25 percent cis-3-hexenol, no detectable trans-2-hexenol, about 49 percent 1-hexanol and about 26 percent hexanals; indicating that linoleic acid provides for good yield of 1-hexanol.

EXAMPLE 7

Turnip leaf material (*Brassica rapa*) is harvested using a Porter-Way greens harvester. The harvested greens are packed on ice in waxed boxes and shipped under refrigeration by truck to a processing site. The plant material is harvested 72 hours prior to processing. To a Kady mill having a 250 gallon working capacity and a 125 hp motor, is added 156.6 gal. of well water at 9° C. and 3.24 lb of linolenic acid (55%, 18:3) from Eastman Chemical Co. The resulting mixture is blended until reaching a temperature of 17° C., at which time 7.6 gal. of Fleischmann's cream yeast (17.1% yeast solids) and 260 lb. of the refrigerated plant material is added. The resulting mixture is subjected to shearing for about 10 minutes. Samples of liquid from the mixture are collected 1, 3, 5 and 10 minutes after shearing is commenced, at which time the temperature of the mixture is 19.1° C., 21.1° C., 23.2° C. and 27.6° C., respectively. Each sample of green juice is filtered through 4 layers of cheesecloth, and the resulting filtrate is allowed to set at room temperature for 1 hour. Each filtrate then is swirled gently, and a 4 ml aliquot is drawn. To each aliquot is mixed 4 ml ethyl acetate, and the resulting mixture is centrifuged. Each organic fraction is analyzed for cis-3-hexen-1-ol using gas chromatographic analysis techniques. The amount of cis-3-hexen-1-ol in the reaction mixture of each sample is determined to be 606 ug, 868 ug, 936 ug and 960 ug, respectively, per gram of plant material processed.

EXAMPLE 8

Into as Osterizer kitchen blender is charged 100 g of a plant material, 12.5 g Fleischmann's cream yeast, 1.65 ml linolenic acid (55%, 18:3) available from Eastman Chemical Co., and 490 ml deionized water. The plant material is fresh Hanover Salad (*Brassica napus*) leaves.

The mixture in the blender, which is about room temperature, is homogenized by operating the blender at high speed setting for about 3 minutes, at which time the homogenate exhibits a temperature of 23° C. The resulting homogenate then is filtered through 4 layers of cheese cloth. The filtrate then is allowed to set for 1 hour. The filtrate then is swirled gently, and a 4 ml aliquot is drawn. To the aliquot is mixed 4 ml ethyl acetate, and the resulting mixture is centrifuged. The organic fraction is analyzed for cis-3-hexen-1-ol using gas chromatographic analysis techniques. The amount of cis-3-hexen-1-ol in the reaction mixture is determined to be 796 ug/g fresh plant material processed.

Similar ingredients, similar in relative amount and similarly blended for 3 minutes, but using 12.5 g Fleischmann's cream yeast which is incubated with stirring at 25–30° C. for 1 hour in the presence of 5 percent of raw, unprocessed molasses, yield cis-3-hexen-1-ol in an amount of 918 ug/g fresh weight of plant material processed.

EXAMPLE 9

Into as Osterizer kitchen blender is charged 100 g of a plant material, 14.6 g Red Star cake yeast, 1.65 ml linolenic acid (55%, 18:3) available from Eastman Chemical Co., and 500 ml deionized water. The plant material is fresh rutabaga leaves (*Brassica napus*, 'American Purple Top') harvested at 65 days after planting.

The mixture in the blender, which is about room temperature, is homogenized by operating the blender at high speed setting for about 2 minutes, at which time the homogenate exhibits a temperature of 25.7° C. The resulting homogenate then is filtered through 4 layers of cheese cloth. The filtrate then is swirled gently, and a 4 ml aliquot is drawn immediately. To the aliquot is mixed 4 ml ethyl acetate, and the resulting mixture is centrifuged. The organic fraction is analyzed for cis-3-hexen-1-ol using gas chromatographic analysis techniques. The amount of cis-3-hexen-1-ol in the reaction mixture is determined to be 252 ug/g fresh plant material processed.

The homogenate is similarly sampled, and extracted with ethyl acetate 15, 30, 45 and 60 minutes after filtration. Those samples yield respective amounts of cis-3-hexen-1-ol of 726, 858, 882 and 876 ug/g fresh weight of plant material processed.

EXAMPLE 10

Into as Osterizer kitchen blender is charged 100 g of a plant material, 14.6 g Fleischmann's cake yeast (29.5% yeast solids), 1.65 ml linolenic acid (55%, 18:3) available from Eastman Chemical Co., and 500 ml deionized water. The plant material is fresh leaves of Chinese Cabbage (*Brassica rapa* 'Pe-Tsai') which are harvested by hand at 121 days after planting.

The mixture in the blender, which is about room temperature, is homogenized by operating the blender at high speed setting for about 2 minutes, at which time the homogenate exhibits a temperature of 21° C. The resulting homogenate then is filtered through 4 layers of cheese cloth. The filtrate then is allowed to set for 1 hour. The filtrate then is swirled gently, and a 4 ml aliquot is drawn. To the aliquot is mixed 4 ml ethyl acetate, and the resulting mixture is centrifuged. The organic fraction is analyzed for cis-3-hexen-1-ol using gas chromatographic analysis techniques. The amount of cis-3-hexen-1-ol in the reaction mixture is determined to be 939.6 ug/g fresh plant material processed.

Similar ingredients, similar in relative amount and similarly blended for 2 minutes, but using 22.6 g of a yeast/water slurry (19.1% yeast solids) made from Fleischmann's cake yeast yield cis-3-hexen-1-ol in an amount of 870 ug/g fresh weight of plant material processed.

Similar ingredients, similar in relative amount and similarly blended for 2 minutes, but using 24.8 g Fleischmann's cream yeast (17.4% yeast solids) yield cis-3-hexen-1-ol in an amount of 866 ug/g fresh weight of plant material processed.

EXAMPLE 11

Into as Osterizer kitchen blender is charged 100 g of a plant material, 14.6 g Red Star cake yeast, 1.65 ml linolenic acid (55%, 18:3) available from Eastman Chemical Co., and 500 ml deionized water. The plant material is a mixture of fresh greens. The greens are composed of leaves of turnip (*Brassica rapa* 'Seven Top'), kale (*Brassica napus* and *B. napus* 'Dwarf Siberian Improved'), and mustard (*Brassica juncea* 'Florida Broadleaf', 'Southern Giant Curled' and 'Old Fashion') harvested 52 days after planting.

The mixture in the blender, which is about room temperature, is homogenized by operating the blender at high speed setting for about 3 minutes, at which time the homogenate exhibits a temperature of 25° C. The resulting homogenate then is filtered through 4 layers of cheese cloth. The filtrate is allowed to set for 1 hour. The filtrate then is swirled gently, and a 4 ml aliquot is drawn. To the aliquot is mixed 4 ml ethyl acetate, and the resulting mixture is centrifuged. The organic fraction is analyzed for cis-3-hexen-1-ol using gas chromatographic analysis techniques. The amount of cis-3-hexen-1-ol in the reaction mixture is determined to be 816 ug/g fresh plant material processed.

Similar materials in similar amounts are processed except that the linolenic acid is replaced by 3.3 ml of raw linseed oil solution treated with lipase in an amount and under conditions sufficient to produce linolenic acid. The lipase is available as Lipase-OF from Meito Sangyo Co., Ltd., and is used as directed by that supplier. That sample yields an amount of cis-3-hexen-1-ol of 781.8 ug/g fresh weight of plant material processed.

EXAMPLE 12

Plant material in the form of Charleston Gray watermelon leaves and vines is harvested by hand 76 days after planting. The foliage, while fresh, is hand cut into about 6 to about 12 inch pieces, and immediately loaded into a Breddo mixer having a 50 gallon working capacity and a 30 hp motor. To 40 lb of leaves and vines is added 5.8 lb Red Star cake yeast, 300 ml linolenic acid (55%, 18:3) from Eastman Chemical Co., and 24 gal. well water at about 20° C. The mixture is blended for 5 min., with 100 ml subsamples being collected at 1 min. intervals. Each subsample is filtered through 4 layers of cheese cloth. The filtrate for each subsample is allowed to set for 1 hour. The filtrate then is swirled gently, and a 4 ml aliquot is drawn. To the aliquot is mixed 4 ml ethyl acetate, and the resulting mixture is centrifuged. The organic fraction is analyzed for cis-3-hexen-1-ol using gas chromatographic analysis techniques. For the subsamples collected at 1, 2, 3, 4 and 5 minute intervals,respectively, the respective amounts of cis-3-hexen-1-ol in the reaction mixture are determined to be 516, 756, 978, 1104 and 1146 ug/g fresh plant material processed.

EXAMPLE 13

Into a Waring Blender at room temperature is mixed 20 g fresh field grown Sultan watermelon foliage, 150 ml tap water, 4.4 g Fleischmann's fresh active cake yeast, and 200 ul linolenic acid obtained from Sigma Chemical. The ingredients are subjected to shearing for 1 minute at high speed setting. The mixture is filtered through 4 layers of cheese cloth, and the green filtrate which is collected is allowed to set for 1 hour at 21° C. Then, 2 ml of the filtrate is extracted with 2 ml diethylether. The amount of cis-3-hexenol is determined by gas chromatographic analysis to be 1677 ug per gram of fresh foliage processed. As such, using the process steps of the present invention, it is possible to obtain a yield of green note compound in excess of about 1500 ug/g plant material employed.

EXAMPLE 14

Into a Waring Blender at room temperature is mixed 50 g fresh field grown Charleston Gray watermelon vine, 150 ml tap water, 8.3 g Fleischrnann's fresh active cake yeast, and 850 ul of lipase treated raw linseed oil (i.e., a source of free unsaturated fatty acid containing approximately 50 percent linolenic acid). The lipase is available as Lipase-OF from Meito Sangyo Co., Ltd., and is used as directed by that supplier. The ingredients are subjected to shearing for 1 minute. The mixture is filtered through 4 layers of cheese cloth, and the green filtrate which is collected is separated into samples which are allowed to set for 1 hour at various temperatures. The temperatures are 21° C., 24.5° C., 31.5° C., 36.5° C. and 44° C. Then, 2 ml of each sample is extracted with 2 ml diethylether. The amount of cis-3-hexenol in each respective sample is determined by gas chromatographic analysis to be 805, 906, 853, 735 and 593 ug per gram of fresh plant material processed.

EXAMPLE 15

Into a Waring Blender at room temperature is mixed 30 g fresh field grown Charleston Gray watermelon foliage, 150 ml tap water, 6.25 g Fleischmann's fresh active cake yeast, and 850 ul of lipase treated raw linseed oil (i.e., a source of free unsaturated fatty acid containing approximately 50 percent linolenic acid). The lipase is available as Lipase-OF from Meito Sangyo Co., Ltd., and is used as directed by that supplier. The ingredients are subjected to shearing for 0.5 minute, during which time the mixture reaches 25.5° C. The mixture is filtered through 4 layers of cheese cloth, and the green filtrate which is collected is allowed to set for 1 hour at room temperature. Then, 2 ml of the filtrate is extracted with 2 ml diethylether. The amount of cis-3-hexen-1-ol in the reaction mixture is determined by gas chromatographic analysis to be 559 ug. Similar ingredients are similarly processed, except that the ingredients are subjected to shearing for 1, 2 and 3 minutes, respectively, during which time the respective mixtures reach 28.5° C., 32° C. and 39° C. The amount of cis-3-hexen-1-ol in each respective mixture is determined by gas chromatographic analysis to be 899, 1063 and 852 ug per gram of fresh plant material processed.

EXAMPLE 16

Into a Waring Blender at room temperature is mixed 30 g fresh field grown watermelon foliage (Sultan) which is cut at 9.5 weeks after planting, 150 ml tap water, 4.4 g Fleischmann's cake yeast and 200 mg linolenic acid (97%, 18:3) obtained from Sigma Chemical which is added during shearing. The ingredients are subjected to shearing for 1 minute at high speed setting. The mixture is strained through cheese cloth, and the green filtrate which is collected is allowed to set under stirring for 15 minutes at room temperature. The amount of cis-3-hexenol is determined by gas chromatographic analysis to be about 100 percent cis-3-hexen-1-ol, with no detectable hexenals, no detectable trans-2-hexenol and no detectable 1-hexanol.

Similar ingredients, similar in relative amount and similarly sheared for 1 minute, but using 200 mg linoleic acid from Sigma Chemical (97% pure) rather than linolenic acid, yields about 35 percent cis-3-hexen-1-ol, no detectable trans-2-hexenol, about 65 percent 1-hexanol and no detectable hexenals; indicating that linoleic acid provides for good yield of 1-hexanol.

For comparison purposes, similar ingredients in relative amounts are similarly processed. However, the fatty acid is linolenic acid and no yeast is incorporated into the reaction mixture. The reaction products include no detectable cis-3-hexen-1-ol or other alcohols, and about 100 percent hexenals.

What is claimed is:
1. A method for providing cis-3-hexen-1-ol, the method comprising the steps of:
   a) providing unsaturated fatty acid;
   b) providing plant biomass having active levels of lipoxygenase and hydroperoxide lyase enzymes;
   c) providing active alcohol dehydrogenase;
   d) providing a mixture by simultaneously contacting the fatty acid, plant biomass and alcohol dehydrogenase in the presence of an aqueous liquid under conditions sufficient to:
      i) provide release of lipoxygenase and hydroperoxide lyase from the plant biomass, and
      ii) provide reaction of the fatty acid with the lipoxygenase, hydroperoxide lyase and alcohol dehydrogenase to provide cis-3-hexen-1-ol;
   e) collecting aqueous phase containing cis-3-hexen-1-ol, such aqueous phase containing greater than 400 ug cis-3-hexen-1-ol per gram of plant biomass provided in step b); and
   f) separating cis-3-hexen-1-ol from the aqueous phase.
2. The method of claim 1 whereby the alcohol dehydrogenase is provided in the form of yeast.
3. The method of claim 1 whereby the fatty acid is linolenic acid.
4. The method of claim 1 whereby the aqueous liquid relative to the plant biomass is an amount of about 3:1 to about 6:1, on a weight basis.
5. The method of claim 1 whereby the fatty acid, plant biomass and alcohol dehydrogenase are contacted in the presence of an aqueous liquid in a continuous manner.
6. The method of claim 1 whereby the plant biomass includes rutabaga foliage.
7. The method of claim 1 whereby the plant biomass includes turnip foliage.
8. The method of claim 1 whereby the plant biomass includes mustard foliage.
9. The method of claim 1 whereby the plant biomass includes watermelon foliage.
10. The process of claim 1 whereby the cis-3-hexen-1-ol collected in step e) is greater than 1000 ug per gram of plant biomass provided in step b).
11. The process of claim 1 whereby the cis-3-hexen-1-ol collected in step e) is greater than 900 ug per gram of plant biomass provided in step b).
12. The method of claim 1 whereby in step d) the mixture is subjected to high shear agitation.
13. The method of claim 12 whereby the mixture is subjected to high shear agitation for less than 5 minutes.
14. The method of claim 1 whereby step e) involves separating liquid portion from plant biomass pulp.
15. The method of claim 14 whereby the liquid portion which is collected is subjected to an incubation time.
16. The method of claim 15 whereby the incubation time does not exceed 60 minutes.
17. The method of claim 1 whereby the linolenic acid is provided in an amount of about 5 to about 10 mg per gram of plant biomass provided in step b).
18. The method of claim 1 whereby the plant biomass provided in step b) is fresh plant material.
19. The method of claim 18 whereby the plant material is employed in step d) within 6 hours after harvest.
20. The method of claim 1 whereby the temperature in step d) is about 15° C. to about 40° C.

* * * * *